(12) United States Patent
Petit et al.

(10) Patent No.: US 10,518,392 B2
(45) Date of Patent: Dec. 31, 2019

(54) RIVETING DEVICE FOR PRECISION ASSEMBLY

(71) Applicant: GILLET GROUP, Nogent (FR)

(72) Inventors: Fabrice Petit, Orcevaux (FR); Pascal Gillet, Nogent (FR)

(73) Assignee: GILLET GROUP, Nogent (FR)

( * ) Notice: Subject to any disclaimer, the term of this patent is extended or adjusted under 35 U.S.C. 154(b) by 217 days.

(21) Appl. No.: 15/553,794

(22) PCT Filed: Feb. 25, 2016

(86) PCT No.: PCT/FR2016/050440
§ 371 (c)(1),
(2) Date: Aug. 25, 2017

(87) PCT Pub. No.: WO2016/135427
PCT Pub. Date: Sep. 1, 2016

(65) Prior Publication Data
US 2018/0029199 A1     Feb. 1, 2018

(30) Foreign Application Priority Data
Feb. 25, 2015 (FR) ...................... 15 51623

(51) Int. Cl.
*B25B 7/06*     (2006.01)
*B25B 7/08*     (2006.01)
(Continued)

(52) U.S. Cl.
CPC ................ *B25B 7/08* (2013.01); *B21J 15/04* (2013.01); *B26B 13/28* (2013.01);
(Continued)

(58) Field of Classification Search
CPC .... B25B 7/08; B25B 7/06; B21J 15/02; B21J 15/04; B21J 15/14; B21J 15/383; B26B 13/28; B26B 17/00; A61B 17/2816
(Continued)

(56) References Cited

U.S. PATENT DOCUMENTS 4,478,532 A * 10/1984 Puro ......................... B25B 7/08
16/342
4,669,340 A * 6/1987 Igarashi ................... B25B 7/10
81/394
(Continued)

FOREIGN PATENT DOCUMENTS

CH     271455 A     10/1950
CN     2103411 U     5/1992
(Continued)

OTHER PUBLICATIONS

International Search Report and Written Opinion dated Jun. 27, 2016 of corresponding International application No. PCT/FR2016/050440; 9 pgs.

*Primary Examiner* — David B Jones
(74) *Attorney, Agent, or Firm* — Maier & Maier, PLLC

(57) ABSTRACT

A riveting device for mutual assembly of two parts each including a bore, where the device includes a non-deformable external rivet having a tubular body suitable for being inserted into said bores and provided on one of the longitudinal ends thereof with a lip, and an internal rivet having a solid deformable cylindrical body and issuing substantially perpendicular from a flange, said tubular body having an external diameter slightly less than the diameter of said bores and a length D between the rear face of the lip thereof and the opposite end thereof at most equal to the sum of the thicknesses of the parts, said cylindrical body having an external homothetic transverse cross-section slightly less
(Continued)

Figure 1:
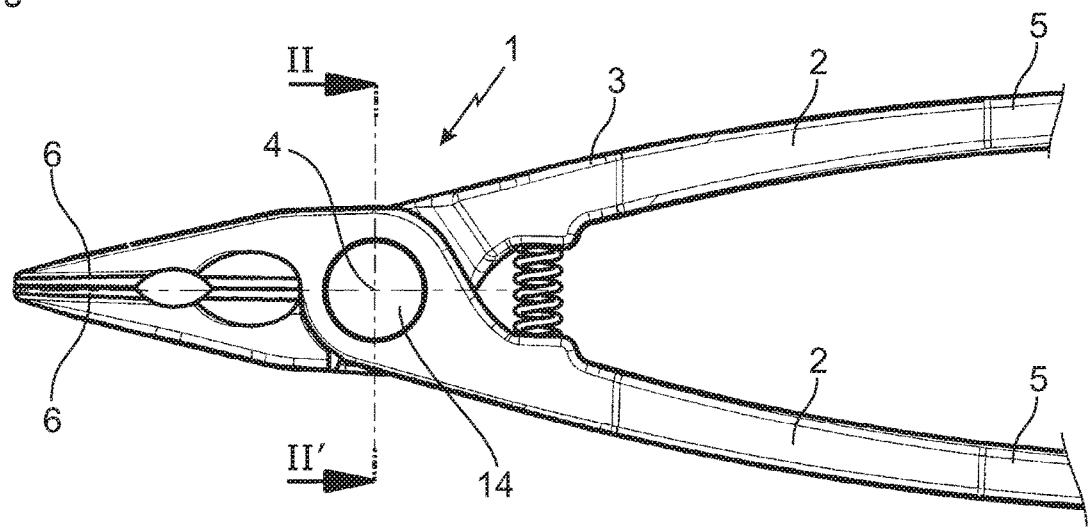

than the internal transverse cross-section of the tubular body, and a length slightly greater than that of the tubular body.

4 Claims, 1 Drawing Sheet

(51) Int. Cl.
*B26B 13/28* (2006.01)
*B21J 15/04* (2006.01)
*B21J 15/14* (2006.01)
*B21J 15/02* (2006.01)
*A61B 17/28* (2006.01)
*B21J 15/38* (2006.01)
*B26B 17/00* (2006.01)

(52) U.S. Cl.
CPC ............ *A61B 17/2816* (2013.01); *B21J 15/02* (2013.01); *B21J 15/14* (2013.01); *B21J 15/383* (2013.01); *B25B 7/06* (2013.01); *B26B 17/00* (2013.01)

(58) Field of Classification Search
USPC ........................................ 81/416; 29/243.521
See application file for complete search history.

(56) References Cited

U.S. PATENT DOCUMENTS

| 5,220,856 A * | 6/1993 | Eggert ...................... B25B 7/06 |
| | | 30/254 |
| 2016/0129561 A1* | 5/2016 | Chen .......................... B25B 7/08 |
| | | 81/417 |

FOREIGN PATENT DOCUMENTS

| DE | 9307010 U1 | 7/1993 |
| DE | 10231369 A1 | 1/2004 |
| EP | 1719589 A1 | 8/2006 |
| FR | 1101870 A | 10/1955 |
| FR | 2715594 A1 | 8/1995 |

* cited by examiner

RIVETING DEVICE FOR PRECISION ASSEMBLY

TECHNICAL FIELD

The present invention relates in general terms to the field of hand tools such as for example wire cutters, pliers or stripping pliers. The invention relates more particularly to a riveting device for precision assembly of the two arms of said hand tool.

PRIOR ART

In the field of hand tools, many models of pliers are already known, comprising two rigid arms articulated on each other about an axis perpendicular to the plane of said arms and forming the handles of said pliers, and a working member at the ends of the arms opposite to those that constitute said handles.

To effect the articulation of the two arms on each other, the use is known of a screw and nut of specific form enabling the arms to be connected while keeping the possibility of pivoting one arm with respect to the other about the longitudinal axis of the screw. To make the arms non-removable, the screw is bonded in the nut. However, this type of assembly is not satisfactory since it requires the often expensive manufacture of a specific screw/nut assembly and a last bonding operation that is difficult to automate.

To overcome the aforementioned drawbacks, using riveting devices such as the one disclosed in the patent application FR 1 363 299 is also known. The riveting device is formed by two parts made from elastically deformable material and comprises firstly an internal rivet with a tubular body and a projecting head and secondly an external rivet with a tubular body and projecting head comprising a core extending inside said body perpendicular to said head, said core having a diameter slightly greater that the inside diameter of the body of the internal rivet, but being shorter. Said tubular body of the external rivet has an outside diameter slightly less than that of the bores of the arms of the pliers to be assembled and an inside diameter no more than the outside diameter of the body of the internal rivet, and has a length at least equal to that of the latter and no more than the sum of the thicknesses of the arms to be assembled. With this configuration of the riveting means, assembly is then obtained by forcibly inserting, in the body of the external rivet, the body of the internal rivet, which will widen under the effect of the core and cause the clamping between the internal and external rivets, the insertion will continue until the heads of said internal and external rivets come into contact with the external faces of the arms to be assembled.

However, this riveting device, which is certainly effective, has several major drawbacks. First of all, the external rivet is particularly complex and therefore expensive to produce. Moreover, the clamping takes place inside the bores of the arms to be assembled so that it is impossible to control it. It is also not possible to control the insertion of the internal rivet in the external rivet and therefore to guarantee correct functioning of the articulation between the arms. Finally, with this type of riveting device, it is not possible to guarantee that there will not be any relative movement of the working members disposed at the ends of the arms opposite to those that constitute the handles. The latter drawback is particularly problematic when said working members are cutting parts that must absolutely be facing each other since, if there has been a relative movement of the working members, it will then be necessary to rework said cutting parts by filing, which is a lengthy and expensive operation preventing any definitive machining of the arms before assembly.

A riveting device like the one disclosed in Chinese utility model 2 103 411 is also known However, this device, which makes it possible to eliminate the distance caused between two blades because of wear by bringing said blades towards each other, cannot therefore guarantee a relative non-movement of the working members disposed at the ends of the arms opposite to those that constitute the handles.

DISCLOSURE OF THE INVENTION

The aim of the present invention is therefore to overcome the aforementioned drawbacks and to propose a riveting device for assembling together two articulated arms of a hand tool with precision, said device guaranteeing perfect functioning of the articulation and the relative non-movement of the working members disposed at the ends of the arms opposite to those that constitute the handles. Furthermore, with the riveting device according to the invention, the arms could be machined definitively before their assembly, allowing rational automation of the process of manufacture of the hand tool.

In accordance with the invention, a riveting device is therefore proposed for assembling together two parts each comprising a bore and being articulated about the axis of said bores, said device comprising a non-deformable external rivet comprising a tubular body with a circular external cross section able to be simultaneously inserted in the bore of the two parts and provided at one of its longitudinal ends with a lip, and an internal rivet comprising a solid cylindrical body able to be inserted inside the tubular body and issuing substantially perpendicularly from a flange, said tubular body having an outside diameter slightly less than the diameter of said bores and a length D between the rear face of its lip and its opposite end slightly greater than the sum of the thicknesses of the parts, said cylindrical body having a homothetic external cross section with dimensions slightly less than the internal cross section of the tubular body, said device being remarkable in that the external rivet is non-deformable and in that the cylindrical body of the internal rivet is deformable in order to crimp the internal rivet on said external rivet and has a length slightly greater than that of the tubular body when the riveting device is placed on the parts to be assembled, that is to say when the rear face of said lip is in contact with one of said parts and the rear face of said flange is in contact with the other one of said parts.

It will be understood clearly that, with such a configuration, the risks related to the clamping together to the two arms, the deformation thereof and the relative movement thereof are in fact non-existent, since only the internal rivet deforms and the separation between the rear faces of the lips and flange is guaranteed by the non-deformable external rivet. It is therefore no longer necessary to repeat the machining of the working members of the hand tool after assembly of its arms together.

The external cross section of said cylindrical body and internal cross section of the tubular body are advantageously circular.

Preferably, the tubular body comprises, on the lip side, a bevel provided along its internal circular edge.

The internal rivet preferably comprises a punch hole on the transverse end face of its cylindrical body opposite to the flange.

SUMMARY DESCRIPTION OF THE FIGURES

Figure 3:
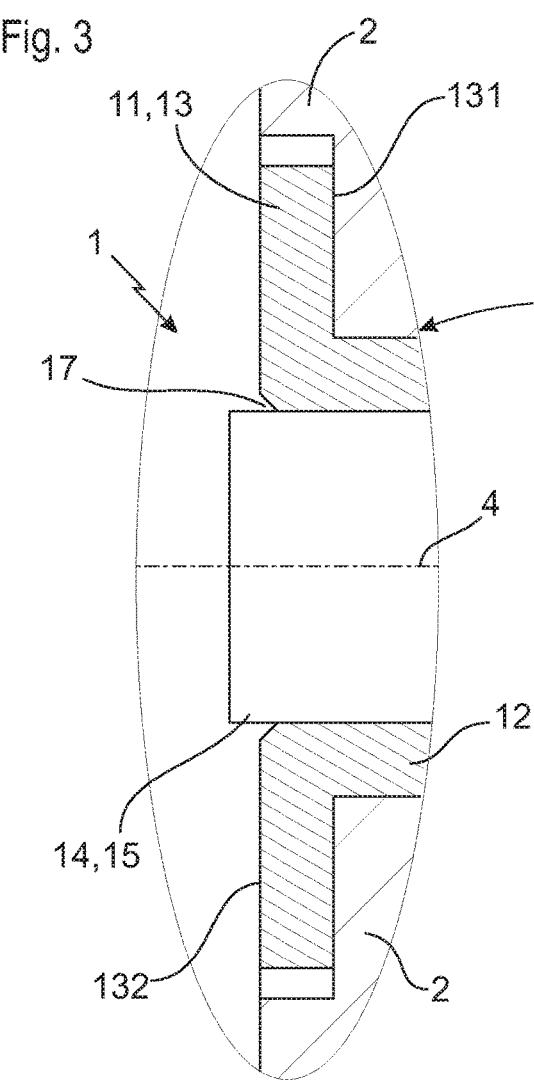
Figure 2:
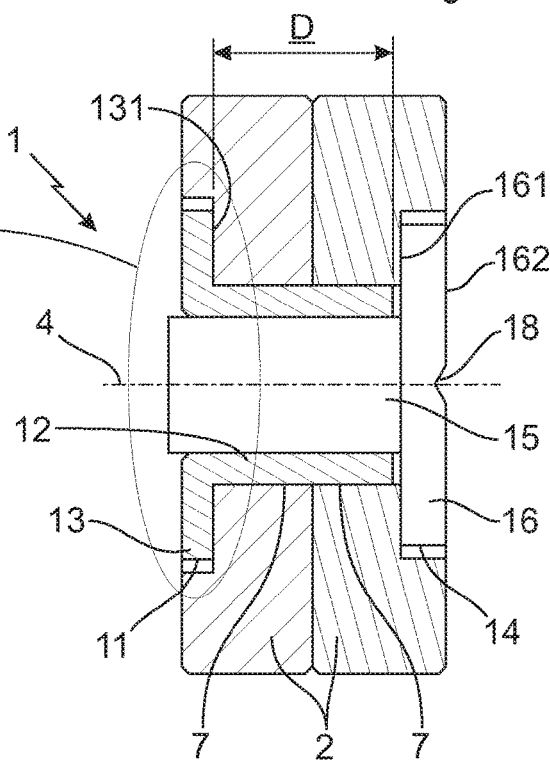

Other advantages and features will emerge more clearly from the following description of a particular example embodiment given by way of non-limitative example, of a riveting device for assembling the articulated arms of a hand tool according to the invention, with reference to the accompanying drawings, in which:

FIG. 1 is a side view of a hand tool, the two articulated arms of which are assembled by the riveting device according to the invention, FIG. 2 is an enlarged cross section of the hand tool of FIG. 1 along the axis XI-II', FIG. 3 is an enlarged view of a detail of FIG. 2.

BEST WAY OF IMPLEMENTING THE TECHNICAL INVENTION

With reference to FIGS. 1 to 3, the riveting device 1 allows assembly between two parts 2 articulated on each other about an axis 4 perpendicular to the plane of said parts 2, the latter being for example two rigid arms 2 of a hand tool 3 forming the handles 5 of said hand tool 3 and each comprising a working member 6 at their end opposite to the one that constitutes the handle 5.

Said riveting device 1 comprises an external rivet 11 comprising a tubular body 12 with a circular external cross section provided at one of its longitudinal ends with a lip 13 roughly annular in shape, and an internal rivet 14 comprising a solid cylindrical body 15 issuing substantially perpendicularly from the rear face 161 of a flange 16 in the general form of a disc.

Here "rear face" means the face of the flange 16 of the internal rivet 14 or of the lip 13 of the external rivet 11 that is situated on the same side as the associated arm 2 when the hand tool 3 is assembled by means of the riveting device 1 according to the invention, and "front face" means the opposite face.

It will be understood clearly that the front face 132 of the lip 13 of the external rivet 11 and or the front face 162 of the flange 16 of the internal rivet 14 are advantageously planar. However, they could also be non-planar, in order to adapt to the parts 2 to be assembled, and be for example frustoconical, without departing from the scope of the present invention.

The outside diameter of the tubular body 12 of the external rivet 11 is slightly less than the diameter of the bores 7 of the arms 2 of the hand tool 3 to be assembled, so as to allow the sliding of said external rivet 11 inside the bores 7. Furthermore, the length D between the rear face 131 of its lip 13 and the opposite end of its tubular body 12 (cf. FIG. 2) is no more than the sum of the thicknesses of the arms 2 to be assembled.

Likewise, the cylindrical body 15 of the internal rivet 14 has firstly an outside diameter slightly less than the inside diameter of the tubular body 12 of the external rivet 11, so as to allow sliding of said internal rivet 14 inside the external rivet 11, and secondly a length slightly greater than that of the tubular body 12 of the external rivet 11 so that, when the riveting device is placed on the parts 2 to be assembled, the internal rivet 14 then being inserted in the external rivet 11 until the respective rear faces 131 and 161 of the lip 13 and of the flange 16 come into abutment against the parts 2, its cylindrical body 15 extends beyond the other end of said tubular body 12 (cf. FIG. 3).

Moreover, the cylindrical body 15 of the internal rivet 14 is deformable and the external rivet 11 is on the other hand non-deformable. Here "non-deformable" means the fact that the associated element is not deformed when it is subjected to the forces used to assemble said riveting device 1.

To do this, the external rivet 11, which is, like the internal rivet 14, preferably metal, undergoes heat treatments so as to prevent any deformation under the action of the forces used to assemble together said external 11 and internal 14 rivets.

A person skilled in the art will have no difficulty in choosing the metals and heat treatment suitable for producing the external 11 and internal 14 rivets according in particular to their dimensions and the forces to be used.

Moreover, the internal cross section of the tubular body 12 of the external rivet 11 and the external cross section of the cylindrical body 15 of the internal rivet 14 may not be circular without departing from the scope of the present invention.

With this configuration, in order to assemble the two arms 2 of the hand tool 3, the following procedure is used:

the external rivet 11 is inserted simultaneously in the bore 7 of each the two arms 2 of the hand tool 3 until the rear face 131 of its lip 13 comes into contact with one of said arms 2, the latter being positioned with respect to each other in accordance with FIG. 1, next the internal rivet 14 is inserted in the tubular body 12 of the external rivet 11 until the rear face 161 of its flange 16 comes into contact with the other one of said arms 2, the free end of the cylindrical body 15 of the internal rivet 14 then projecting slightly from the lip 13 of the external rivet 11, finally a pressure is exerted, by means of the tool of a press, on the free end of the cylindrical body 15 of the external rivet 11, the other end of which on the flange 16 side is in abutment on the frame of the press, in order to deform it so as to create a rim in order to crimp the internal rivet 14 on the external rivet 11 and thus effect the assembly together of the two arms 2 of the hand tool 3.

It will be understood clearly that, with the riveting device 1 according to the invention, only the free end of the cylindrical body 15 deforms, which makes it possible to control the deformation operation and to guarantee the correct functioning of the articulation of said arms 2 since the external rivet 11 is non-deformable under the action or the forces used and the outside diameter of its tubular body 12 remains invariable and guarantees the necessary clearance for the correct functioning of the articulation of said arms 2.

Moreover, the parts 2 are not clamped together since only the cylindrical body 15 is deformable and the quantity of material to be deformed, in order to provide the clamping between the external 11 and internal 14 rivets, is minimal, namely the free end of the cylindrical body 15 of the internal rivet 14 then projecting slightly from the external rivet 11. It is therefore necessary for the press to be adjusted so that its compression force is just sufficient for the tool to be able to deform only the free end of the cylindrical body 15 and for the progression of said tool to stop when it comes into contact with the lip 13 of the external rivet 11. This is because, since the external rivet 11 is non-deformable and therefore stronger than the cylindrical body 15, it would be necessary to use a compression force slightly higher than that necessary for the deformation of the free end of the cylindrical body 15, which is not possible because of the adjustment of the press.

With this configuration of the riveting device 1, it is possible to obtain a very precise assembly of the two arms 2 since said outside diameter of the tubular body 12 of the external rivet 11 can be achieved with a precision of around $1/100^{th}$ of a millimetre.

Thus the risks related to the clamping of the two arms 2 together, to their deformation and to their relative movement are in fact non-existent, since the forces are exerted only on the free end of the cylindrical body 15 of the internal rivet 14 and the separation between the rear faces of the lips 13 and flange 6 is guaranteed by the non-deformability of the external rivet 11.

The riveting device 1 makes it possible to avoid any reworking of the working member 6 of the hand tool 3 after assembly of its arms 2 together, and therefore to be able to automate the manufacture of the hand tool 3 by assembling its arms 2 of the end of their final machining.

Likewise, the non-deformable external rivet 11 avoids any unwanted deformation of the internal rivet 14, that is to say other than that of the free end of its cylindrical body 15.

To facilitate the deformation of said free end of the cylindrical body 15, the tubular body 12 comprises, on the lip 13 side, a bevel 17 provided along its internal circular edge.

Finally, the front face 162 of the flange 16 of the internal rivet 14 preferably comprises a punch hole 18 making it possible to correctly position the riveting device 1 under the press tool when said internal rivet 14 is crimped on the external rivet 11.

INDUSTRIAL APPLICABILITY

It will be understood clearly that the riveting device according to the invention can be used for any type of tool other than a hand tool 3 of the pliers or similar type. Likewise, it is quite obvious that the riveting device 1 according to the invention can be adapted to assemble two parts articulated on each other or not and belonging to any other type of technical mechanism such as for example a motor or a lift.

Finally, it goes without saying that the examples of a riveting device 1 according to the invention that has just been described are merely particular illustrations, in no case limitative of the invention.

The invention claimed is:

1. A riveting arrangement for assembling together two articulated parts each comprising a bore, said two parts being articulated about the axis of said bores, said arrangement comprising:
    an external rivet comprising a hollow tubular body with a circular external cross section configured to be simultaneously inserted in the bore of the two parts and a lip arranged at one longitudinal end of a plurality of longitudinal ends of the hollow tubular body, said tubular body having an outside diameter slightly less than the diameter of said bores and a length D between a rear face of the lip and a longitudinal end opposite of said lip no more than the sum of the length of the bore of the two parts, and
    an internal rivet comprising a solid cylindrical body configured to be inserted inside the hollow tubular body of the external rivet and a flange arranged perpendicularly at one of a plurality of longitudinal ends of the solid cylindrical body, said cylindrical body having an external cross section with a shape that is homothetic to the shape of an internal cross section of the hollow tubular body and with dimensions slightly less than the said internal cross section
    wherein the external rivet is non-deformable and the cylindrical body of the internal rivet is deformable in order to crimp the internal rivet on said external rivet and has a length greater than that of the tubular body when the riveting device is placed on the parts to be assembled when the rear face of said lip is in contact with one of said parts and a rear face of said flange is in contact with the other one of said parts.

2. The riveting arrangement according to claim 1, wherein the external cross section of said cylindrical body and internal cross section of the tubular body are circular.

3. The riveting arrangement according to claim 1, wherein the tubular body comprises, on a lip side, a bevel provided along an internal circular edge.

4. The riveting arrangement according to claim 1, wherein the internal rivet comprises a punch hole on a front face of the flange.

* * * * *